United States Patent [19]

Hood, III

[11] Patent Number: 5,887,755
[45] Date of Patent: Mar. 30, 1999

[54] WOUND SEALANT PREPARATION AND APPLICATION DEVICE AND METHOD

[75] Inventor: Andrew G. Hood, III, Redwood City, Calif.

[73] Assignee: Quantic Biomedical Partners, Redwood City, Calif.

[21] Appl. No.: 898,374

[22] Filed: Jul. 21, 1997

Related U.S. Application Data

[63] Continuation of Ser. No. 472,941, Jun. 6, 1995, abandoned.
[51] Int. Cl.$^6$ ................................................ B67D 5/52
[52] U.S. Cl. .................. 222/135; 222/145.5; 222/195; 222/394; 239/427.5
[58] Field of Search ...................... 222/135, 137, 222/145.2, 145.5, 148, 195, 386, 394; 239/427.5

[56] References Cited

U.S. PATENT DOCUMENTS

| | | | |
|---|---|---|---|
| 2,158,593 | 5/1939 | Scrimgeour | 128/221 |
| 3,179,107 | 4/1965 | Clark | 128/221 |
| 3,556,348 | 1/1971 | Bristow | 222/137 |
| 3,595,467 | 7/1971 | Goglio | 222/494 X |
| 4,040,420 | 8/1977 | Speer | 128/218 |
| 4,083,474 | 4/1978 | Waite | 222/145 |
| 4,109,653 | 8/1978 | Kozam et al. | 128/218 |
| 4,359,049 | 11/1982 | Redl et al. | 128/218 |
| 4,629,455 | 12/1986 | Kanno | 604/241 |
| 4,631,055 | 12/1986 | Redl et al. | 604/82 |
| 4,735,616 | 4/1988 | Eibl et al. | 604/191 |
| 4,743,229 | 5/1988 | Chu | 604/82 |
| 4,842,581 | 6/1989 | Davis | 604/38 |
| 4,874,368 | 10/1989 | Miller et al. | 222/137 X |
| 4,902,281 | 2/1990 | Avoy | 604/191 |
| 4,978,073 | 12/1990 | von Eckardstein | 239/427.5 X |
| 4,978,336 | 12/1990 | Capozzi et al. | 604/82 |
| 4,979,942 | 12/1990 | Wolf et al. | 222/145.5 X |
| 4,986,443 | 1/1991 | Saur et al. | 222/82 X |
| 5,116,315 | 5/1992 | Capozzi et al. | 222/137 X |
| 5,185,001 | 2/1993 | Galanakis | 604/5 |
| 5,219,097 | 6/1993 | Huber et al. | 222/145.2 |
| 5,484,107 | 1/1996 | Holmes | 239/427.5 |
| 5,585,007 | 12/1996 | Antanavich | 210/782 |

FOREIGN PATENT DOCUMENTS

| | | | |
|---|---|---|---|
| 2558209 | 7/1985 | France . | |
| 2661097 | 10/1991 | France . | |
| 4223356 | 1/1994 | Germany | 222/137 |

OTHER PUBLICATIONS

Sierra, D.H., "Fibrin Sealant Adhesive Systems: A Review of Their Chemistry, Material Properties and Clinical Applications," *J. Biomat. App.* 7:309–352 (1993).

*Primary Examiner*—Joseph A. Kaufman
*Attorney, Agent, or Firm*—Skjerven, Morrill, MacPherson, Franklin & Friel, LLP; Laura Terlizzi; Bradford P. Schmidt

[57] ABSTRACT

The present invention provides a preparation and application device useful for mixing and dispensing a plurality of fluids, wherein the fluids must be mixed immediately prior to use. In one embodiment, the device includes two fluid delivery systems connected to a manifold having two separate fluid channels. Each fluid channel conducts fluid to a mixing chamber, from which, following mixing, the mixture of fluids is dispensed. The manifold additionally includes a gas channel having an outlet connected to one of the fluid channels, which can be used to supply a pressurized gas to the mixing chamber to expel the mixture from the chamber, reducing the likelihood that the mixture can clog the device. The invention also provides a method for preparing and dispensing a mixture of two fluids.

20 Claims, 3 Drawing Sheets

WOUND SEALANT PREPARATION AND APPLICATION DEVICE AND METHOD

This application is a continuation of application Ser. No. 08/472,941, filed Jun. 6, 1995 now abandoned.

BACKGROUND OF THE INVENTION

1. Field of the Invention

The present invention relates to a device and method for mixing a plurality of fluids and dispensing the resultant mixture, wherein a gas is used to force the mixture out of the device. In particular, the present invention relates to a device and method for preparing and dispensing a wound sealant.

2. Description of the Related Art

A number of applications require the mixing of a plurality of fluids immediately before use of the mixture. Examples of such fluids include the components of "fibrin glue" wound sealants, gel components for use in electrophoresis, and the components of epoxy cement. In each of these applications, the components must be combined in appropriate amounts, thoroughly mixed to form a mixture, and dispensed before increased viscosity impairs mixture flow. The basic considerations associated with mixing separate components and immediately dispensing the mixture are exemplified herein by a discussion of the preparation of wound sealants.

Wound sealants are used in the repair of damaged tissues and vessels. In particular, wound sealants are designed to prevent persistent fluid loss from or into a wound, which can increase patient discomfort and morbidity, prolong recovery, and compromise or prevent an otherwise successful outcome.

The problem of fluid leakage is particularly severe in highly vascularized tissues, such as kidney, liver, spleen and cancellous bone, which continue to bleed even after electrocautery. Arterial vascular grafts often leak at sites of anastomosis, along suture lines, and even through the grafts. Dural wounds are extremely difficult to repair, with a 30% failure rate for some of the best currently available procedures. Resection of lung tissue often results in persistent air leaks, which significantly prolong recovery. Moreover, such problems are often exacerbated in patients suffering from diabetes or other disease processes that impair normal wound healing.

The use of wound sealants based on fibrin glue has received widespread attention as a solution to the problem of fluid leakage. Fibrin glue is formed by using a fibrinogen activator, such as thrombin, to cleave fibrinogen to fibrin, followed by formation of a coagulum by fibrin-fibrin crosslinking. Fibrin molecules also form crosslinks with collagen, a principle constituent of most tissues. These fibrin-collagen crosslinks promote adherence of the fibrin clot to the tissue to be sealed.

This approach offers a number of advantages. First, fibrin glues can be prepared from a patient's own blood, thus eliminating the problems of disease transmission and immunological complications associated with the use of donor materials. Second, the rate of coagulum formation can be adjusted to suit the needs of a particular application by adjusting the concentration of fibrinogen activator in the mixture.

Third, fibrin glues are predominantly physiologic in origin, and therefore normal fibrinolytic processes remove the coagulum, typically, within two to three weeks, leaving minimal scarring. If desirable, coagulum breakdown can be slowed by the addition of antifibrinolytics such as ε-amino caproic acid, tranexamic acid, or aprotinin. Finally, other chemical agents, such as antibiotics or anticancer drugs, can be added to the fibrinogen and or fibrinogen activator solutions before mixing to provide sustained release of the agent at a wound site or selected site of action.

While the benefits of fibrin glue wound sealants are clear, the preparation and use of fibrin glues is complicated by several problems. For example, thorough mixing is required to form a strong adhesive. However, a limited time period is available for mixing, given that coagulation begins immediately upon contact of the fibrinogen solution with the fibrinogen activator solution.

In addition, fibrin glues are typically applied using a syringe-like applicator, in which the coagulating mixture must flow through a relatively small aperture. Any interruption in the flow of the mixture, which is often necessary during wound sealing, can result in formation of a coagulum that plugs the aperture. When this happens, treatment can be continued only by replacing the applicator or, in some devices, clogged applicator parts.

Examples of this type of applicator are disclosed U.S. Pat. No. 4,359,049 (issued Nov. 16, 1982 to Redl et al.) and U.S. Pat. No. 4,735,616 (issued Apr. 5, 1988 to Eibl et al.). In these devices, two syringes are attached at their outlets to a connecting head that provides a separate fluid channel for the contents of each syringe. Mixing occurs in a mixing needle attached to the outlets of the two channels. Clogging of the needle during interruptions in use causes difficulties when a patient requires more than one continuous application of fibrin glue. One embodiment disclosed in U.S. Pat. No. 4,359,049 has a spraying head, rather than a mixing needle, wherein a spray is produced by sterile gas supplied at the outlet of each of the fluid channels.

A variation of this device, described in U.S. Pat. No. 4,631,055 (issued Dec. 23, 1986 to Redl et al.), has a connecting head adapted to connect either to a mixing needle or a multi-lumen catheter. The connecting head includes a third fluid channel for a gas. Each of the channels is designed connect to a separate lumen of the catheter. Thus, fluids in the three channels come together at the inlet of the mixing needle or at the outlet of the catheter.

This design was intended to allow the application of fibrin glue in the form of a liquid or fine spray by varying the relative flow rates of fibrinogen, fibrinogen activator, and gas. However, in practice, a sputtering effect, rather than a fine, even spray, is observed. Furthermore, the catheter embodiment suffers from the disadvantage that mixing occurs in an uncontrolled manner after the fluid streams exit the catheter.

Thus, current preparation and application devices for fibrin glue wound sealants often do not provide adequate mixing of the fibrinogen and fibrinogen activator solutions or do not provide a mechanism for smooth application of the wound sealant mixture. Furthermore, these devices suffer from clogging problems that prevent further use after an interruption in the application process.

SUMMARY OF THE INVENTION

The present invention comprises a device having a manifold for mixing a plurality of fluids and applying the resultant mixture. The manifold includes an inlet end having first and second inlets and an outlet end opposite the inlet end having first and second outlets. First and second fluid channels extend from the first and second inlets to the first and second outlets. A gas channel extends from a third inlet and terminates at and is continuous with the first fluid channel. In one embodiment, a one-way valve is positioned in the line providing gas. In another embodiment, the one-way valve is attached to a gas inlet fitting in the manifold.

In one embodiment, the device is used to mix and dispense a wound sealant. The wound sealant preparation and application device of the present invention combines appropriate amounts of a plurality of fluid components, provides vigorous mixing action, and rapidly dispenses the resultant mixture. Furthermore, the gas channel provides a purge feature that expels any mixture remaining in the device to ensure that the device does not become clogged during interruptions in use.

DETAILED DESCRIPTION OF THE INVENTION

Figure 1:
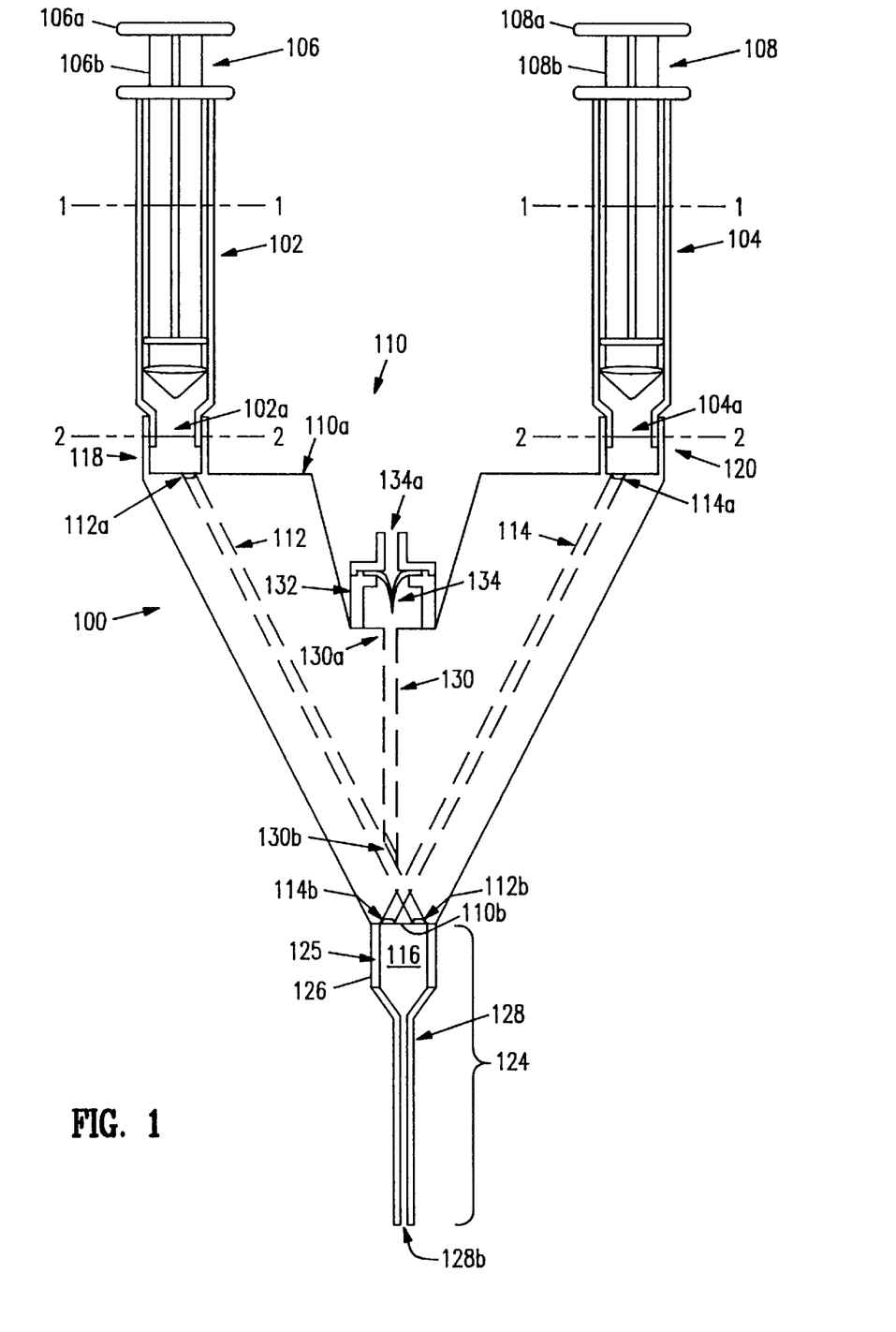
FIG. 1 is longitudinal cross-section of a device according the present invention.

FIG. 1 shows a preparation and application device 100 (hereinafter device 100) useful for dispensing a mixture of a plurality of fluids, wherein the plurality of fluids is mixed to form a viscous mixture immediately before use. The viscous mixture is exemplified herein by a fibrin glue wound sealant. As shown in FIG. 1, device 100 includes a plurality of fluid delivery systems, syringes 102, 104 removably connected to a manifold 110 having a plurality of separate fluid channels 112, 114, i.e., one fluid channel for each fluid delivery system. Each fluid delivery system is coupled to a fluid channel which conducts fluid from the fluid delivery system to a mixing chamber 116 at a predetermined volume flow rate. Upon mixing in mixing chamber 116, the plurality of fluids form the desired viscous mixture. The relationship of the plurality of fluid channels 112, 114 and of mixing chamber 116 ensures that vigorous mixing occurs in mixing chamber 116.

In addition, device 100 includes a purge system that ejects any residual mixture during interruptions in use of device 100, thereby preventing the residual mixture from clogging device 100. The present invention also provides an application system for use in device 100 as well as a method for preparing and dispensing a mixture of a plurality of fluids.

Referring to FIG. 1, device 100 includes syringes 102, 104, which are the fluid delivery systems in this embodiment and eject fluid through syringe outlets 102a, 104a, respectively. The sizes of syringes 102, 104 and corresponding syringe outlets 102a and 104a may be the same or different. In one embodiment, syringes 102, 104 have identical lengths, but have different cross-sectional areas at lines 1—1. When device 100 is used to prepare and apply fibrin glues, syringes 102, 104 generally have a cross-sectional area ratio of about 10:1 or greater. In a variation of this embodiment, outlets 102a, 104a of syringes 102, 104 also have proportionately different cross-sectional areas at lines 2—2. Thus, if syringes 102, 104 have a cross-sectional area ratio at line 1—1 of 10:1, syringe outlets 102a, 104a also have a cross-sectional area ratio at line 2—2 of 10:1.

Although the fluid delivery systems are syringes in FIG. 1, those skilled in the art recognize that syringes 102 and 104 can be replaced with any system capable of ejecting a predetermined amount of fluid. For example, the fluid delivery system can include tubing connected to a pressurized fluid source.

In general, it is desirable to eject fluids through syringe outlets 102a, 104a substantially simultaneously. Substantially simultaneous fluid ejection can be achieved using syringes 102, 104 (FIG. 1) by positioning syringes 102, 104 close enough to allow the user to depress plungers 106, 108 simultaneously with one hand, using the thumb and heel of the hand. Alternatively, device 100 can include a common activation mechanism for the fluid delivery systems. Suitable common activation mechanisms do not differ from those known in the art. For example, suitable common activation mechanisms for syringes 102, 104 include a part linking plungers 106, 108, such as an adaptor that fits over the ends 106a, 108a of plungers 106, 108 or a nonflexible bridge linking the plunger stems 106b, 108b of plungers 106, 108. If depression of the plungers is automated, device 100 can include a common timing control unit that activates plungers 106, 108 substantially simultaneously.

If the fluid delivery systems include tubing connected to pressurized fluid sources, the common activation means can include manual push-button type valves positioned in the flowpath between the pressurized fluid sources and the fluid system outlets, wherein the valves are operably linked so that pushing a button activates flow from each of the pressurized fluid sources substantially simultaneously. Alternatively, the common activation means can include a common timing control unit that activates substantially simultaneous flow from the pressurized fluid sources.

Syringes 102, 104 (FIG. 1) are removably connected to fluid inlet fittings 118, 120 positioned on a manifold inlet end 110a of manifold 110 at fluid channel inlets 112a, 114a. Fluid inlet fittings 118, 120 couple syringes 102, 104, respectively, to fluid channels 112, 114, respectively. Fluid inlet fittings 118, 120 can be any type of joining piece that forms a fluid-tight seal between manifold 110 and syringes 102, 104 and provides fluid communication between syringes 102, 104 and fluid channels 112, 114, respectively. Fluid inlet fittings 118, 120 can be extensions of manifold 110 or separate pieces mounted on manifold 110. When a syringe is used for fluid delivery as illustrated in FIG. 1, the corresponding inlet fitting can include a mechanism that forms a positive connection with the syringe, such as a luer taper that fits into a luer taper on the syringe tip. Alternatively, the mechanism can be interlocking, such as, for example, luer lock ears that engage a luer fitting on the syringe.

Manifold 110 also has manifold outlet end 110b opposite manifold inlet end 110a, with fluid channel outlets 112b, 114b of fluid channels 112, 114 located in manifold outlet end 110b. Fluid channels 112, 114 extend from fluid channel inlets 112a, 114a, respectively, to fluid channel outlets 112b, 114b, respectively.

The size and shape of manifold 110 is dictated by the particular application. The embodiment shown in FIG. 1 is suitable for use in dispensing a fibrin glue. Therefore, device 100 is small enough to facilitate one-handed operation, and manifold inlet end 110a is wider than manifold outlet end 110b. In particular, manifold inlet end 110a is sufficiently wide to facilitate connection of a plurality of syringes. The syringes can be eccentric syringes, facilitating locating fluid inlet fittings 118, 120 closer together than with regular syringes. Manifold outlet end 110b is suitably sized to accommodate a delivery spout 124 containing mixing chamber 116, which is described more fully hereinafter.

Manifold 110 additionally includes gas channel 130, with gas channel inlet 130a and gas channel outlet 130b. In FIG. 1, gas channel inlet 130a is located on manifold inlet end 110a. However, the location of gas channel inlet 130 is not critical and can vary with the design of manifold 110. In particular, gas channel inlet 130a can be located at any convenient position on manifold 110 that does not interfere with connection of syringes 102, 104 to manifold 110 and facilitates suitable positioning of gas channel 130.

Gas channel 130 terminates at and is continuous with fluid channel 112 at outlet 130b, which is closer to fluid channel outlet 112b than to fluid channel inlet 112a. In particular, gas channel outlet 130b is sufficiently close to fluid channel outlet 112b so that fluid channel 112 does not become clogged by contact with the mixture of fluids in mixing chamber 116, as described in more detail hereinafter.

In one embodiment, gas channel outlet 130b is sufficiently close to fluid channel outlet 112a to facilitate intermittent operation of device 100. During interruptions in preparation and application of a fluid mixture such as a fibrin glue, gas exiting gas channel outlet 130b fills a portion of channel 112 between gas channel outlet 130b and mixing chamber 116. This volume is preferably small, to avoid substantial dilution of fluid in fluid channel 112 with gas, which could otherwise alter the ratio of fluid mixture components when operation begins again. In general, gas channel outlet 130b is located so that not more than about one-tenth to about two-tenths of the volume of fluid channel 112 is contained in the portion of fluid channel 112 between gas channel outlet 130b and mixing chamber 116.

Device 100 also includes gas inlet fitting 132 positioned on manifold 110 at gas channel inlet 130a and one-way valve 134 positioned in gas inlet fitting 132. Gas inlet fitting 132 can be any type of joining piece that forms a gas-tight seal between manifold 110 and a pressurized fluid source. Like fluid inlet fittings 118, 120, gas inlet fitting 132 can be separate from or part of the manifold.

One-way valve 134 is positioned to communicate with gas channel 130 so as to provide gas flow from gas channel inlet 130a to gas channel outlet 130b only. One-way valve 132 can be connected to gas inlet fitting 132, as shown in FIG. 1, or positioned at any point along the route of the gas from its source to gas channel 130. One-way valve 134 includes a mechanism at one way valve inlet 134a to provide gas-tight coupling to a pressurized gas source, as described more fully hereinafter.

Delivery spout 124 is positioned on manifold outlet end 110b. In the embodiment illustrated in FIG. 1, delivery spout 124 contains an annulus 126 and a catheter 128. Annulus 126 has an inner surface that serves as a wall 125 of mixing chamber 116. Delivery spout 124 can be formed as a unitary part of manifold 110 or can be removably connected to manifold 110. In addition, catheter 128 can be part of or removably connected to delivery spout 124. Catheters are readily connected to devices using various types of connectors. For example, the delivery spout can form a luer taper for attachment of a catheter hub. As one skilled in the art understands, other fluid applicators can be used instead of a catheter. In particular, catheter 128 can be replaced with a spray jet-type nozzle.

Figure 2A:
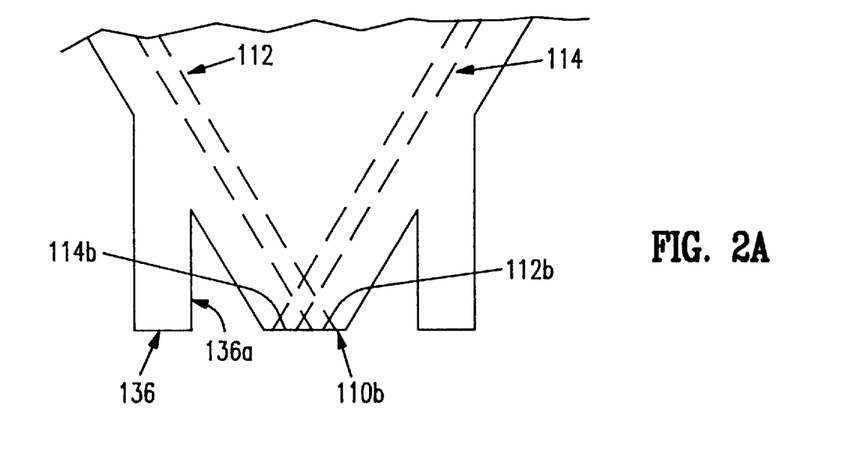
FIGS. 2A and 2B show portions of another embodiment of the device of FIG. 1.

An embodiment of device 100 wherein manifold 110 is designed for removably connecting delivery spout 124 is illustrated in FIG. 2A. In this embodiment, manifold outlet end 110b is a tapered region containing fluid channel outlets 112b, 114b that is encircled by spout fitting 136. Although manifold 110 is illustrated as tapered in this embodiment, one of skill understands that the shape of the manifold is not critical. Spout fitting 136 is adapted to removably engage a catheter hub. The tapered region can be a luer taper, or, alternatively, spout fitting 136 can be threaded on an interior wall 136a for engagement of a luer lock catheter. In this embodiment, the interior of the catheter hub forms mixing chamber 116 when the catheter is connected to manifold outlet end 110b.

Figure 2B:
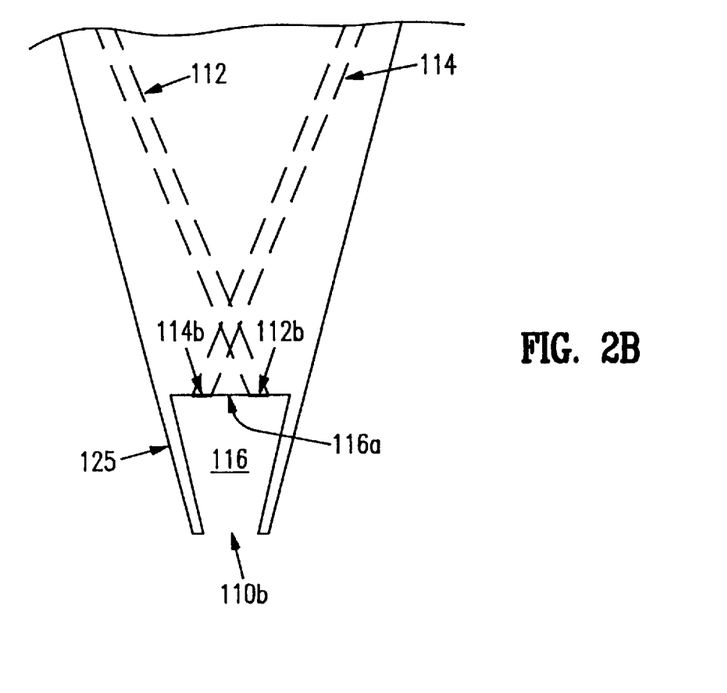

Another embodiment of device 100 wherein manifold 110 is designed for removably connecting delivery spout 124 is illustrated in FIG. 2B. In this embodiment, manifold outlet end 110b is a tapered region that forms mixing chamber 116. Fluid channel outlets 112b, 114b terminate at and are continuous with mixing chamber inlet end 116a. Wall 125 of mixing chamber 116 is adapted to removably engage a catheter hub. In the embodiment illustrated in FIG. 2B, wall 125 forms a luer taper. A spray jet-type nozzle or other fluid application system can be used in place of a catheter. In the embodiment illustrated in FIG. 2B, engagement of a catheter or other fluid application system to the manifold forms the delivery spout.

Referring again to FIG. 1, fluid channel outlets 112b, 114b communicate with mixing chamber 116 so that fluid streams ejected from fluid channel outlets 112b, 114b enter mixing chamber 116. The fluid streams mix in mixing chamber 116 and exit catheter 128 through catheter outlet 128b.

Figure 3:
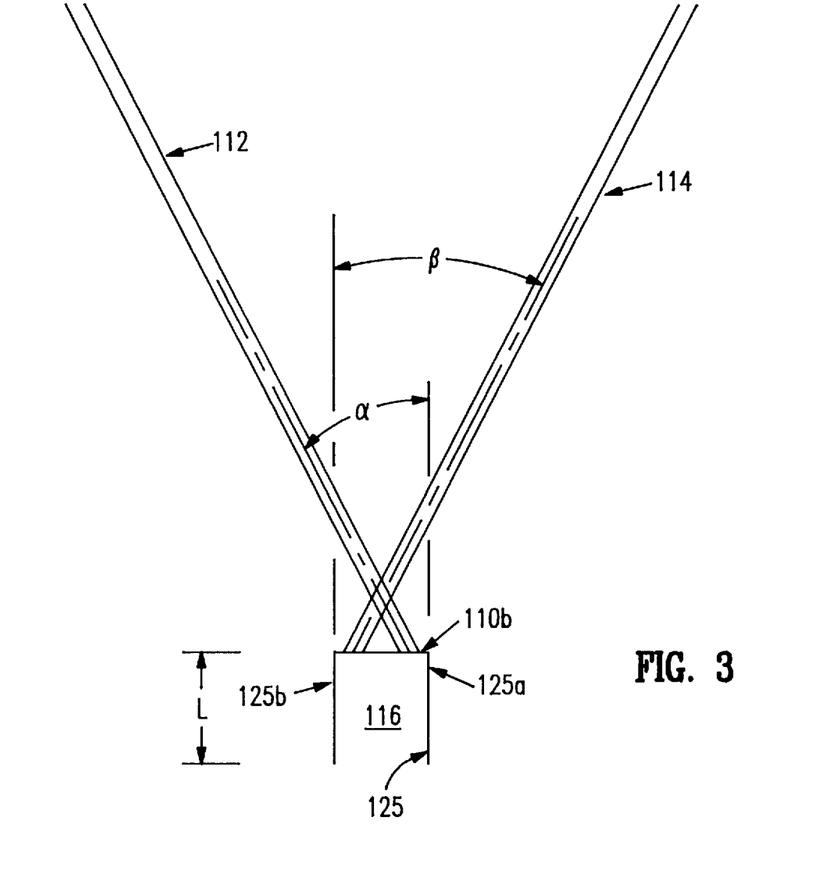
FIG. 3 illustrates the positioning of a plurality of fluid channels with respect to a mixing chamber according to the principles of the present invention.
Figure 4:
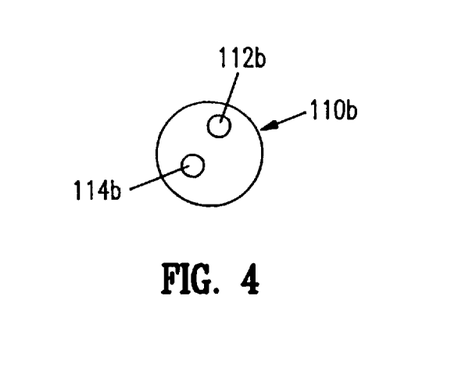
FIG. 4 shows a view of an outlet end of a manifold of the device of FIG. 1 that illustrates the relative positions of a plurality of fluid channel outlets.

FIGS. 3 and 4 illustrate the locations of fluid channels 112, 114 and fluid channel outlets 112b, 114b relative to mixing chamber 116 in one embodiment. Referring to FIG. 3, fluid channels 112, 114 do not intersect, but rather cross over one another in different planes. A center line through fluid channel 112 intersects a wall portion 125a of mixing chamber 116 at an angle $\alpha$. Another wall portion 125b of mixing chamber 116 is substantially opposite wall portion 125a, and a center line through fluid channel 114 intersects wall portion 125b at an angle $\beta$. Angles $\alpha$ and $\beta$ can be the same or different, and are illustrated in FIG. 3 as substantially the same angle. FIG. 4 is a transverse section through manifold outlet end 110b showing the location of fluid channel outlets 112b, 114b in the embodiment pictured in FIG. 3.

The arrangement of fluid channels 112, 114 and fluid channel outlets 112b, 114b relative to mixing chamber wall portions 125a and 125b described in FIGS. 3 and 4 ensures that fluid streams exiting fluid channel outlets 112b and 114b are not parallel in a common plane. Angles $\alpha$, $\beta$ are selected so that fluid streams exiting fluid channel outlets 112b, 114b contact wall portions 125a, 125b, respectively, at a sufficient angle to provide vigorous, swirling mixing. In addition, angles $\alpha$, $\beta$ are selected so that fluid streams exiting fluid channel outlets 112b, 114b contact wall portions 125a, 125b, respectively, so as to provide sufficient mixing of the fluids prior to ejection of the fluid mixture from mixing chamber 116. Typically, angles $\alpha$, $\beta$ are selected so that the fluid streams contact wall portions 125a, 125b at a distance from manifold outlet end 110 that is one-third or less the length "1" of mixing chamber 116 (FIG. 3). Those skilled in the art are able to determine suitable angles $\alpha$, $\beta$, depending on fluid viscosity, fluid flow rate, and the size and shape of mixing chamber 116. Regarding mixing chamber 116, the chamber can be tapered or contain grooves or ridges to enhance mixing.

Those of skill will also recognize that the shape of the manifold is not critical so long as the manifold is a sufficient length to support fluid channels 112 and 114 at angles α and β and that the inlet end of the channels is spaced to facilitate one-handed operation and attachment of two syringes of suitable sizes.

The portions of the device of this invention that contact fluid in operation should be inert to the fluid contacted. For many applications, including dispensing a wound sealant, the fluid delivery systems can include syringes made of a plastic such as polycarbonates, polyurethane, acrylics, ABS polymers, polysolfone, and the like. The inlet fittings, manifold, and nozzle can be made of a similar material. The device is made by conventional methods such as injection molding using wires or pins to provide the channels.

The application device and method of the present invention are particularly useful for dispensing fluid mixtures wherein the mixing of a plurality of fluids results in an increase in viscosity sufficient to impair mixture flow. The operation of the application device of the present invention is exemplified herein by the use of the device to prepare and dispense a coagulum-based wound sealant, e.g. a fibrin glue.

As described above, such wound sealants are prepared by mixing a procoagulant-containing solution (which contains fibrinogen) with a solution comprising a fibrinogen activator. Any procoagulant-containing solution useful in preparing prior art wound sealants can be used with the application device, as exemplified herein by a fibrinogen-containing solution. Although the following description relates to a solution containing fibrinogen, other procoagulant proteins, and cellular components of whole blood such as platelets, white cells, and buffy coat can be included in fibrinogen-containing solution. Suitable fibrinogen-containing solutions are typically obtained from plasma separated from anticoagulated whole blood by density difference fractionation (e.g., by gravity or centrifugation). Generally, the fibrinogen content of such solutions is between about 2 mg/ml to about 50 mg/ml.

Fibrinogen activators are well known and include thrombin and batroxobin, both of which are commercially available. In particular, bovine thrombin is available from a variety of sources including Armour and Parke-Davis.

In the presence of excess fibrinogen, the rate of coagulum formation after mixing fibrinogen with fibrinogen activator is directly dependent on the final concentration of fibrinogen activator in the mixture. Typically, the final concentration ranges from about 10 to 100 Units/ml. At a concentration of 100 Units/ml, a coagulum forms in about three to five seconds; at 50 Units/ml, coagulum formation occurs in about 15–20 seconds; and at 10 Units/ml, a period of about 60–120 seconds is required for coagulum formation.

A variety of additional components can be added to the fibrinogen or fibrinogen activator solutions to modify the characteristics of the coagulum. Antifibrinolytics can be employed to regulate the time required for the body to break down the coagulum. Platelets can be included in the fibrinogen solution to increase coagulum strength and adhesion, augment hemostasis, and improve healing. Additionally, calcium can be added to the fibrinogen activator solution to accelerate fibrin crosslinking and stability. Ground bone, demineralized bone matrix, hydroxyapatite, or the like can be included in the fibrinogen activator solution to promote bone regrowth. Furthermore, pharmacologic agents, such as, for example, antibiotics, can also be added to the fibrinogen activator solution.

The volume ratios of the two solutions are important in determining the strength and adhesiveness of the wound sealant. Fibrinogen solution to fibrinogen activator solution volume ratios of about 5:1 have been successfully employed. However, the incidence of unsatisfactory results is greater than with higher ratios. Ratios of from about 10:1 to about 12:1 are reliably effective. Ratios higher than 12:1 make thorough mixing of the two solutions more difficult and less reliable.

The application device of the present invention facilitates the simultaneous delivery of different amounts of the two solutions. In one embodiment, for example, the fluid delivery systems include syringes having the same length, but differing cross-sectional areas.

Referring to FIG. 1, to dispense a fibrin glue-based wound sealant, gas channel 130 is coupled to a pressurized source of sterile medical gas via flexible tubing connected to gas inlet fitting 132. Medical gas includes any gas suitable for use in a medical procedure, such as air or oxygen. Gas flow can be commenced at any time before, or simultaneously with, the depression of plungers 106, 108. In embodiments where it is not desirable to mix gas with the fluids, gas flow is commenced after cessation of depression of plungers 106, 108. A fibrinogen solution is introduced into syringe 102, which is coupled to fluid channel 112 via fluid inlet fitting 118. A fibrinogen activator solution is introduced into syringe 104, which is coupled to fluid channel 114 via fluid inlet fitting 120.

Pressure is then applied substantially simultaneously to plungers 106, 108, causing the solutions in syringes 102, 104 to flow into fluid channels 112, 114. The two solutions flow through their respective fluid channels to meet in mixing chamber 116. As fibrinogen solution reaches gas channel outlet 130, the fibrinogen solution mixes with gas and this mixture then flows into mixing chamber 116.

Admixing the fibrinogen solution with gas before mixing with the fibrinogen activator solution prevents sputtering that occurs with currently available devices that mix all three components together at the same point in the device. In addition, if gas channel outlet 130b is located close to mixing chamber 116, the gas stream exiting gas channel outlet 130b helps prevent the thrombin solution from migrating into fluid channel 112, thereby preventing the formation of a coagulum that could clog fluid channel 112. Fluid channel 114 does not clog because the fibrinogen concentration in the channel is too low.

The fibrinogen-gas mixture and the fibrinogen activator solution enter mixing chamber 116 in streams at an angle to each other and at an angle to wall 125 of delivery spout 124, which imparts a swirling motion to the streams, thus promoting the vigorous mixing necessary for a complete reaction between the fibrinogen and thrombin. The mixture is then ejected through catheter 128 under pressure due to a combination of the depression of plungers 106, 108 and gas flow through gas channel 130.

After a sufficient amount of the mixture has been applied to a target surface, the pressure on plungers 106, 108 is stopped substantially simultaneously. Sterile medical gas continues to flow along gas channel 130 into the end of fluid channel 112 near fluid channel outlet 112b, thereby purging any residual fibrinogen solution from the end of fluid channel 112 and any of the coagulating mixture remaining in mixing chamber 116. This feature of the application device ensures that the mixture is cleared from the device before coagulation progresses far enough to clog mixing chamber 116 or catheter 128. In this manner, device 110 can support intermittent use without requiring cleaning or replacement of parts.

In the event that the pressure in mixing chamber 116 exceeds the pressure in gas channel 130 during depression of plungers 106, 108, one-way valve 134 prevents reflux of the fibrinogen solution along gas channel 130.

The present invention also provides a method for preparing and dispensing a mixture of a plurality of fluids. The method includes admixing a first fluid with a pressurized gas to form a first fluid-gas mixture; vigorously mixing the first fluid-gas mixture with a second fluid in a mixing chamber to form a second fluid-gas mixture; and rapidly dispensing the second fluid-gas mixture through an opening in the mixing chamber.

The second fluid-gas mixture may be dispensed by ejecting a stream of the mixture through the opening or by ejecting a spray of the mixture through the opening. After a sufficient amount of the second fluid-gas mixture has been dispensed, the mixing chamber is purged of the second fluid-gas mixture by flowing pressurized gas through the mixing chamber. After the mixing chamber has been purged, the dispensing step can optionally be repeated.

In one embodiment, the mixture to be dispensed is a fibrin glue, the first fluid includes fibrinogen, and the second fluid includes a fibrinogen activator. The pressurized gas is a sterile medical gas. In a variation of this embodiment, the fibrinogen activator is thrombin.

EXAMPLE 1

Preparation of a Wound Sealant Preparation and Application Device

An exemplary wound sealant preparation and application device of this invention was prepared as follows. A manifold similar to that illustrated in FIG. 1 and having a mixing chamber similar to that illustrated in FIG. 2B was made from an acrylic block obtained from TAP Plastics, San Rafael, Calif. The dimensions of the plastic formed into a manifold were as follows. The inlet end and the outlet end of the manifold were each about 40 mm in length with the center-to-center distance between the fluid inlet fittings being about 24 mm. The manifold was approximately 58 mm in length and 10 mm in depth. Fluid inlet fittings and the wall forming the mixing chamber were attached to and extended from the manifold. The length of the mixing chamber (measured as illustrated in FIG. 3) was 22 mm. The wall housing the mixing chamber formed a luer taper for attachment of a catheter or other fluid application system. A one-way valve was affixed to a gas inlet fitting grooved into the manifold between the fluid inlet fittings.

The fluid channels were each about 60 mm in length and 1 mm in diameter. The center-to-center distance between the fluid channel outlets in the top of the mixing chamber was about 2 mm. Therefore, angles $\alpha$ and $\beta$ were each about 12°. The gas channel intersected with the first fluid channel about 8 mm from the outlet of the channel, so that less than 15% of the volume in the fluid channel is ejected by gas exiting the gas channel.

The gas and fluid channels were drilled in the manifold using fabricating equipment (Dremel Moto-Tool Model 395-5, Racine, Wis.). The one way valve (catalog no. 325452, Vernay Labs, Yellow Springs, Ohio) was affixed to the gas channel to allow gas to flow through the gas channel toward the junction with the first fluid channel.

A catheter tip (2.1 mm×83 mm Angiocath, catalog no. 38-2832, Deseret Medical Inc., Beckton Dickenson & Co., Sandy, Utah) with a luer taper was connected to the wall housing the mixing chamber to form the delivery spout. Syringes (Monoject syringes: MJ12 12 cc syringe, catalog no. 325452 and MJtb 1 cc tuberculin syringe, catalog no. 309626, both from Sherwood Medical, St. Louis, Mo.) were used as the fluid delivery assemblies. In another embodiment, a 1 cc tuberculin syringe from Beckton Dickenson & Co., Sandy, Utah (catalog no. 309626) was used.

In another embodiment, a spray nozzle (Sprayco, Detroit, Mich.) was used in place of the catheter as the delivery spout.

EXAMPLE 2

Preparation of an Alternate Embodiment of the Device of Example 1

An alternate embodiment of the Device of Example 1 was prepared as follows. Using fabricating equipment (Dremel Moto-Tool Model 395-5, Racine, Wis.), a hole (1 mm in diameter) was drilled in a manifold similar to that illustrated in FIGS. 1 and 2A (DUOFLO manifold, Hemaedics, Pacific Palisades, Calif.) to form a gas channel that connected with a first fluid channel about 10 mm from the outlet end of the first fluid channel. A one way valve (catalog no. 325452, Vernay Labs, Yellow Springs, Ohio) was affixed to the third channel to allow gas to flow through the third channel toward the junction with the first fluid channel.

A catheter tip (2.1 mm ×83 mm Angiocath, catalog no. 38-2832, Deseret Medical Inc., Beckton Dickenson & Co., Sandy, Utah) with a luer taper was attached to form the delivery spout. Syringes were used as the fluid delivery assemblies as described in Example 1.

EXAMPLE 3

Preparation of a Wound Sealant

A fibrin glue wound sealant was prepared as follows, using the device of Example 2 having the catheter as the delivery spout. The gas channel was connected to a medical air container having a gas line fitted with a $0.2\mu$ filter. The 12 cc syringe was filled with fibrinogen solution (bovine plasma concentrated using a hemoconcentration ultrafiltration unit (Minntech Corp., Minneapolis, Minn.) to provide a fibrinogen concentration of 3.5 mg/ml) and the 1 cc syringe was filled with thrombin solution (THROMBINAR, 1,250 U/ml, Armour Pharmaceuticals, Kankakee, Ill.).

Both syringe barrels were depressed simultaneously and fibrin glue was ejected from the delivery spout. The glue formed a coagulum within about 5 seconds of ejection.

Table 1 illustrates the ratio of the cross-sectional areas of the syringe barrels used.

TABLE 1

| Syringe | Diameter* | Area** | Ratio:MJ12 |
|---|---|---|---|
| MJ12 | 16 | 201 | 1:1 |
| BDtb | 4.7 | 17.3 | 1:11.6 |
| MJtb | 4.8 | 18.3 | 1:11.0 |

*in mm; **in mm$^2$

Of the ratios illustrated in Table 1, use of either tuberculin syringe provided suitable relative volumes of fibrinogen solution and thrombin solution to form a fibrin glue from a thrombin solution and a fibrinogen solution having the concentration used in this example.

Table 2, below, illustrates the starting and diluted values (following mixing) for fibrinogen solution and thrombin solution. The fibrinogen solution (bovine plasma) was diluted with physiologic saline to form the various starting fibrinogen concentrations. The thrombin solution was diluted with water.

TABLE 2

| Syringe Pair | Original Concentration | | Final Concentration | |
|---|---|---|---|---|
| | Thrombin (U/ml) | Fibrinogen (mg/dl) | Thrombin (U/ml) | Fibrinogen (mg/dl) |
| MJ12/MJ12 | 200 | 700 | 100 | 350 |
| | 100 | 700 | 50 | 350 |
| | 20 | 700 | 10 | 350 |
| | 200 | 350 | 100 | 175 |
| | 200 | 150 | 100 | 75 |
| MJ12/BDtb | 1250 | 700 | 99 | 644 |
| | 500 | 700 | 40 | 644 |
| | 100 | 700 | 8 | 644 |
| | 1250 | 350 | 99 | 322 |
| | 1250 | 150 | 99 | 138 |

Using the two 12 cc syringes and thrombin and fibrinogen concentrations illustrated in Table 2, the first three coagula formed were soft, and the last was runny and did not set. Using the 12 cc and tuberculin syringes, the first three coagula were very firm, the third was firm and the last formed a soft coagulum.

What is claimed is:

1. A device for mixing a plurality of fluids and applying the resultant mixture, said device including a manifold comprising:
   an inlet end having first and second inlets and an outlet end opposite said inlet end having first and second outlets;
   first and second fluid channels extending from said first and second inlets to said first and second outlets, respectively; and
   a gas channel extending from a third inlet and terminating at an outlet wherein said outlet is continuous with a wall of said first fluid channel wherein said gas channel does not extend to the outlet end of said manifold.

2. The device of claim 1 wherein said manifold has a center axis that extends from said inlet end to said outlet end and said first and second fluid channels each cross said center axis in different planes.

3. The device of claim 1 wherein said gas channel outlet is located at a position in said first fluid channel closer to said first outlet than to said first inlet.

4. The device of claim 3 wherein said gas channel outlet is located at a position in said first fluid channel at about one-tenth of the length of said first fluid channel from said first outlet.

5. The device of claim 1 additionally comprising first and second fluid inlet fittings on the inlet end of said manifold positioned at the first and second inlets, respectively, said first and second fluid inlet fittings adapted to couple first and second fluid delivery systems, respectively, to said first and second fluid channels, respectively.

6. The device of claim 5 additionally comprising first and second fluid delivery systems coupled to said first and second inlet fittings, respectively, wherein said first and second fluid delivery system are adapted to controllably provide a first and second fluid, respectively, to said first and second fluid channels, respectively.

7. The device of claim 6 wherein said first and second fluid delivery systems comprise syringes.

8. The device of claim 6 wherein said first syringe has a length identical to said second syringe and a cross-sectional area at least ten times larger than the cross-sectional area of said second syringe.

9. The device of claim 1 additionally comprising a gas inlet fitting on said manifold at said gas channel, said gas inlet fitting adapted to couple a pressurized gas source to said gas channel.

10. The device of claim 1 additionally comprising a delivery spout attached to said outlet end of said manifold, said outlets of said first and second fluid channels positioned so that fluid streams exiting said first and second fluid channels are deflected by substantially opposing regions of the inner surface of said delivery spout.

11. The device of claim 10 wherein said delivery spout is removably attached to said manifold.

12. The device of claim 11 wherein a fluid application system attached to the outlet end of the manifold forms the delivery spout.

13. The device of claim 12 wherein the fluid application system is selected from the group consisting of a catheter and a spray jet nozzle.

14. A device for mixing a plurality of fluids and applying the resultant mixture, said device comprising:
   a manifold comprising:
      an inlet end and an outlet end opposite said inlet end;
      first and second inlets located in said inlet end and first and second outlets located in said outlet end;
      first and second fluid channels extending from said first and second inlets to said first and second outlets, respectively; and
      a gas channel extending from a third inlet in said inlet end and terminating at an outlet wherein said outlet is continuous with a wall of said first fluid channel wherein said gas channel does not extend to the outlet end of said manifold;
   a one way valve positioned in said gas channel;
   first and second fluid inlet fittings on the inlet end of the manifold positioned at the first and second fluid channel inlets, respectively, said first and second fluid inlet fittings adapted to removably connect to first and second syringes, respectively;
   first and second syringes removably connected to said first and second inlet fittings, respectively so that said first syringe is capable of providing a first fluid to said first fluid channel, and said second syringe is capable of providing a second fluid to said second fluid channel;
   a mixing chamber positioned on the outlet end of said manifold so that fluid streams exiting said first and second fluid channels are deflected by opposing regions of the mixing chamber; and
   a delivery spout for delivering fluids from the mixing chamber to a target.

15. A method for preparing and dispensing a mixture of a plurality of biological fluids comprising:
   (a) admixing a first biological fluid with a pressurized gas to form a first biological fluid-gas mixture;
   (b) vigorously mixing said first biological fluid-gas mixture with a second biological fluid in a mixing chamber to form a second biological fluid-gas mixture, wherein the second biological fluid-gas mixture develops a viscosity greater than the first biological fluid-gas mixture; and
   (c) ejecting a stream of said second biological fluid-gas mixture through an opening of said mixing chamber before said second biological fluid-gas mixture can plug the opening.

16. The method of claim 15 additionally comprising, after dispensing a desired amount of said second biological fluid-gas mixture, purging said mixing chamber of said second biological fluid-gas mixture by flowing pressurized gas through said mixing chamber.

17. The method of claim 16 additionally comprising, after purging said mixing chamber, repeating operations (a)–(c) of claim 15.

18. The method of claim 15 wherein said pressurized gas is a sterile medical gas.

19. The method of claim 18 wherein said first biological fluid includes fibrinogen and said second biological fluid includes a fibrinogen activator.

20. The method of claim 19 wherein said fibrinogen activator is thrombin.

* * * * *